United States Patent [19]

Hofke

[11] Patent Number: 4,672,973

[45] Date of Patent: Jun. 16, 1987

[54] DEVICE AND METHOD FOR DETERMINING SKIN TYPE

[75] Inventor: Fred Hofke, East Greenville, Pa.

[73] Assignee: Revlon, Inc., New York, N.Y.

[21] Appl. No.: 767,078

[22] Filed: Aug. 20, 1985

Related U.S. Application Data

[63] Continuation of Ser. No. 472,781, Mar. 3, 1983, abandoned.

[51] Int. Cl.⁴ ............................................... A61B 5/00
[52] U.S. Cl. .................................................... 128/665
[58] Field of Search ............... 128/664, 665, 760, 757, 128/759; 436/71; 356/364–370

[56] References Cited

U.S. PATENT DOCUMENTS

| Re. 31,879 | 5/1985 | Lubbers et al. | 128/665 X |
| 3,648,685 | 3/1972 | Hepp et al. | 128/665 |
| 4,170,987 | 10/1979 | Anselmo et al. | 128/665 |
| 4,267,844 | 5/1981 | Yamanishi | 128/665 X |
| 4,370,986 | 2/1983 | Gebhart et al. | 128/665 X |
| 4,392,498 | 7/1983 | Leveque et al. | 128/664 X |
| 4,398,541 | 8/1983 | Pugliese | 128/665 |
| 4,414,980 | 11/1983 | Mott | 128/664 |
| 4,442,844 | 4/1984 | Navach | 128/664 X |

FOREIGN PATENT DOCUMENTS 57-90161 6/1982 Japan .................................... 128/760

Primary Examiner—Edward M. Coven

[57] ABSTRACT

A battery-operated device and method for determining the skin type of a living subject is disclosed in which an oil sample carried by a probe is subjected to the impingement of an essentially monochromatic light source of predetermined wavelength. The amount of light passing through the oil sample is detected and an output current proportional thereto is produced. This output current is amplified and drives a meter which displays the skin type of the subject. Calibration means and a method for calibrating the meter utilizing an oil-free probe are disclosed, as well as a means for adjusting the bandwidth of the output of the amplifier to coincide with the meter.

16 Claims, 2 Drawing Figures

DEVICE AND METHOD FOR DETERMINING SKIN TYPE

CROSS REFERENCE TO RELATED APPLICATIONS

This application is a continuation of application Ser. No. 472,781, filed Mar. 3, 1983, now abandoned.

This application is related to the following applications, each of which is assigned to the assignee of this application and each of which was filed concurrently herewith:

"Probe For Device For Determining Skin Type"; and

"Improved Device for Determining Skin Type".

BACKGROUND OF THE INVENTION

The present invention relates generally to apparatus and method for determining the skin type of an individual, and more particularly, to electronic apparatus utilizing a light source which is transmitted through an oil sample taken from the skin of an individual.

As is well known in the cosmetics, dermatology and pharmaecutical fields, a film or deposit of natural oil is present on the skin surface of a person. The formation of this oil film and its deposition on the skin is governed by the sebaceous glands which become active at about the time of puberty and continue to increase in activity until the person reaches the early twenties. Thereafter, the sebaceous glands then slowly diminish in efficiency and thus, the degree of oiliness of the skin is lessened as the person ages. It is also generally known that aged skin is a drier skin, e.g., less oil content.

Skin type may be divided into three broad categories with respect to skin oil content: (1) normal; (2) oiler than normal; and (3) drier than normal. Specific skin care and make-up products are designed to conform and to perform their functions according to skin type.

To determine an individual's skin type, a dermatologist will generally visually observe the patient's skin and relate the condition to the patient's age. Dermatologists also examine the skin surface for shininess as well as ease of transference of skin oil to a glass slide or test paper. The presence or absence of selected pathologic findings, such as blackheads, redness, scaling and the location of same, also contribute to a reasonably accurate determination of skin type.

To date, no reliable instrumentation has been available which will provide a truly objective evaluation and determination of the skin type of an individual either by physicians or lay persons, e.g., cosmetologists.

Conventional apparatus for measuring the amount of oil or sebum secreted by the skin of a living subject generally fall into two classes. One such class of devices is described in U.S. Pat. No. 4,224,950, to Bore et al, wherein the change in transparency of a glass plate due to oil adhering thereto is measured. The other class of devices are those which typically use chemical analysis methods, such as diffusions, gas chromatography and, as disclosed by Tur et al, U.S. Pat. No. 3,906,933, electrostatically charged printing surfaces which obtain an imprint of the skin. However, the drawback of this second class of devices is that although they may be intended for use by unskilled personnel, an analytical evaluation must later be conducted by skilled personnel, which evaluation is both costly and time consuming.

The device described in U.S. Pat. No. 4,224,950 to Bore et al is a sebumeter which is intended to evaluate the activity of the sebaceous glands by means of a sample of the sebum secreted by the skin in the vicinity of the forehead. This device comprises a casing for holding a removable sample-holder which projects from the casing. A translucent element carried by the sample-holder can be applied to the forehead of the subject. A scale is located within the casing and carries at least one reference mark which, upon illumination of the translucent element by means of a self-contained light source, enables the user of the device to read, by observation of the reference mark, the amount of sebum deposited on the sample-holder.

While such a device may be useful for determining the amount of sebum on the skin surface of one individual, some difficulty and a great deal on inconvenience arises when the glass plate used therewith must be changed. In addition, the device disclosed therein is mechanical in nature and is subject to mechanical failure, particularly the calibrated compression spring which is secured to the sample-holder. Another drawback of the Bore et al device is that it requires a certain period of time during which the user of the device must observe the location of the reference mark in order to determine the amount of sebum present on an individual's skin. Finally, due to the size of the Bore et al device, it is subject to easily being damaged when used at cosmetic counters, either by being dropped onto the counter, or onto the floor around the counter, where it may be subjected to crushing by salespersons or customers.

When a device for determining skin type is to be utilized by untrained or unskilled personnel, such as cosmetic counter salespersons, it is necessary that means be provided within the device such that accurate readings can be easily obtained. This is especially true with electronic devices which may be sensitive, to ambient temperature, line voltage variations, battery life, rough handling, variations in probe construction, etc. The present invention is therefore provided with a calibration circuit to insure that accurate readings are continuously obtained with the subject skin type determining device. The method of calibrating the disclosed device is simple, rapid and accurate and thus is ideally suited for use by untrained or unskilled users.

Another conventional but non-relevant device is shown in U.S. Pat. No. 3,241,431 to Brutten et al, and discloses method and apparatus for the measurement of fingerprint density by measuring the opacity of a strip of translucent material carrying a fingerprint. The method of calibrating this device is complex and time consuming and therefore susceptible to error.

In the cosmetic field, it is desirable that customers receive prompt and accurate answers so that the greatest number of customers can be evaluated within any given time period thereby maximizing the sales of cosmetics to these customers.

SUMMARY AND OBJECTS OF THE INVENTION

In view of the foregoing, it should be apparent that there still exists a need in the art for apparatus and method for reliably determining the amount of oil on the skin surface of a living individual in a simple and low cost manner and which may be readily used to easily determine the skin type of that individual. It is, therefore, a primary object of this invention to provide apparatus for accurately analyzing a person's skin oil sample which is characterized by its ease of calibration and use.

More particularly, it is an object of this invention to provide a device for use by untrained or unskilled personnel for determining skin type which employs a probe for receiving a sample of oil from a person's skin.

Still more particularly, it is an object of this invention to provide a method and means which will accurately determine a person's skin type by using light transmission measurement elements.

Another object of the present invention is to provide method and apparatus for determining a person's skin type which is of rugged construction, simple to use and which is low in cost to manufacture.

Still another object of the present invention is to provide a device for determining skin type which is portable and battery-powered so that it can be placed on a counter top and moved from place to place without wire cords or the like.

Briefly described, these and other objects of the present invention are accomplished by providing a device which accepts a plastic probe containing an oil sample taken from the skin of an individual whose skin type is to be determined. An essentially monochromatic beam of light is transmitted through the probe which is received by a light receptor arranged on the opposite side of the probe. The signal from the light receptor is amplified and used to drive display means which indicate the skin type of the individual from whom the oil sample was obtained. A calibration circuit is provided with the device so that when a clean probe is employed the display will be calibrated at zero or dry. Separate batteries are used to power the light source and the light receptor, amplifier and calibration circuits.

The method aspects of the present invention comprise the steps of detecting that portion of said impinging essentially monochromatic light which is transmitted through said probe, producing an output current proportional to the amount of the detected light, and displaying said output current to indicate the type of skin of the subject being tested.

DETAILED DESCRIPTION OF THE PREFERRED EMBODIMENT

Figure 1:
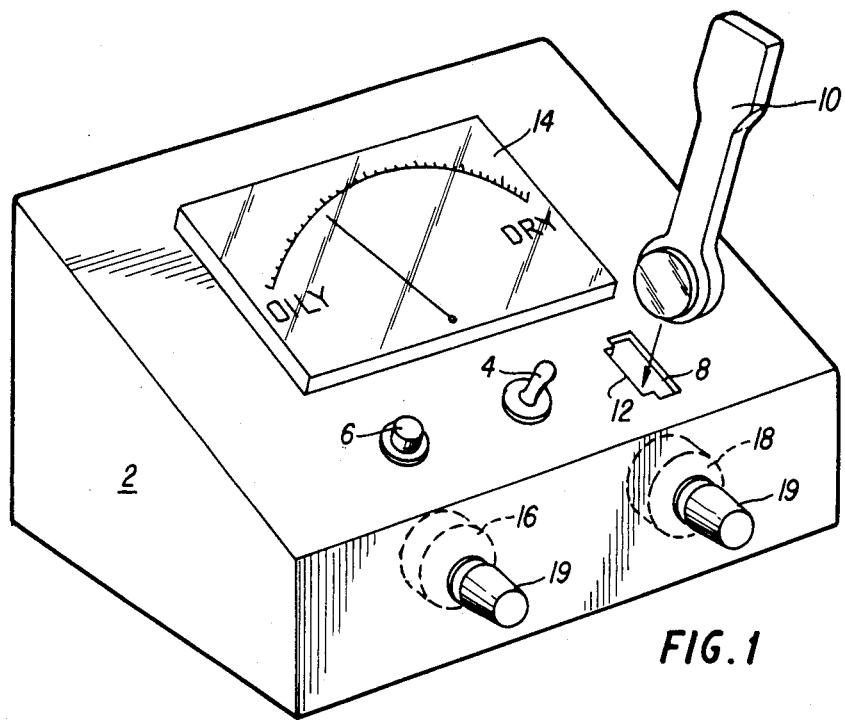
FIG. 1 is a perspective view showing the device for determining skin type of the present invention.

Referring now in detail to the drawings wherein like parts are designated by like reference numerals throughout, there is illustrated in FIG. 1 a housing 2 into which the various components of the inventive device is positioned for determining skin type. A power switch 4 is provided for powering the photoreceptor, display and calibration circuits. A record power switch 6 is also provided on the front face of case 2 for powering the light source. A master power switch 5 (shown in FIG. 2) provides master power control for the device.

A slot 8 is also provided on the front face of the case 2 for receiving a removable probe 10 which carries the oil sample from the skin of the individual being evaluated. The slot 8 includes a key 12 which insures that the probe 10 is inserted into the slot 8 with the correct orientation. Probe 10 is preferably made of plastic and of the type as more fully described in commonly assigned co-pending application Ser. No. 472,548, filed concurrently herewith entitled "Probe For Device For Determining Skin Type", the subject matter of which is incorporated herein by reference.

A meter 14 is provided on the front face of the case 2 for displaying the determined skin type. The meter, which may preferably be a 0–50 microammeter, is calibrated from "oily" at one end of the scale to "dry", at full pointer deflection at the other end of the scale. Alternately, instead of a scale with grid marks, color bands could be utilized. Furthermore, any suitable display means, such as light emitting diodes, could be used in place of the meter 14.

A meter calibration control 16 and a light receptor control 18 may be provided on the front side of the case 2. Alternately, the light receptor bandwidth control 18 may be provided on the rear side of the case 2 since once set, it is not usually necessary for the operator of the device to adjust the output bandwidth of the light receptor. Knobs 19 may be provided for each of the controls 16 and 18.

Figure 2:
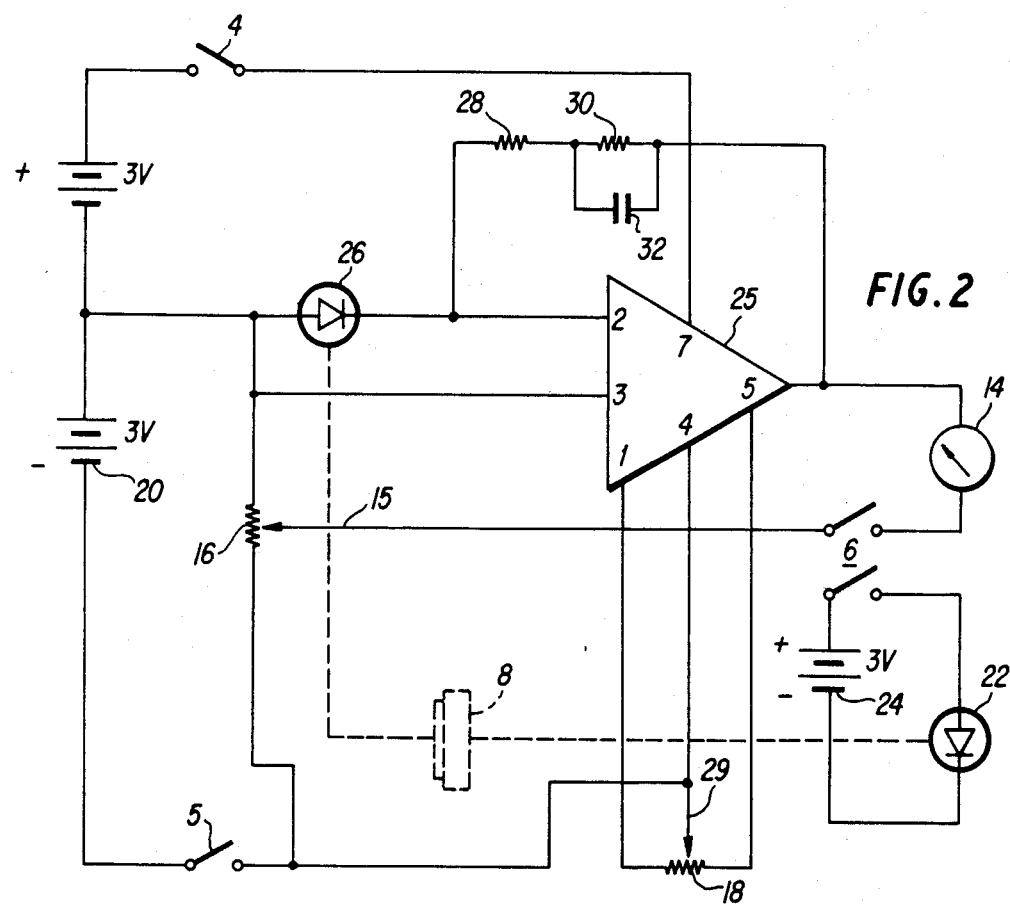
FIG. 2 is a schematic diagram of the circuitry of the present invention.

FIG. 2 shows the electrical schematic diagram of the instant device for determining skin type. Four 1.5 volt batteries 20 are utilized to power all circuits except for the light source 22, which is independently powered with a pair of 1.5 volt batteries 24. As shown, master power switch 5 is connected at one pole to the negative pole of the main battery 20 and at its other pole to both one pole of the meter calibration control potentiometer 16 and also to the wiper 29 of the light receptor bandwidth control potentiometer 18.

A power switch 4 is connected between the positive pole of the main battery 20 and pin 7 of an IC amplifier 25 which may be a CA 3130T, manufactured by Sylvania, RCA, Texas Instruments, and others.

The input of a light receptor 26 is connected at a point A between the two pairs of batteries which form the main battery 20, as well as one pole of the meter calibration potentiometer 16. One input of the amplifier 25 is also connected at point A. The output of the light receptor 26 is connected to the second input of the amplifier 25. The light receptor 26 may preferably be any suitable photodiode or similar device whose output is capable of being amplified by the amplifier 25 such that is it capable of driving the meter 14 which is connected to the output of the amplifier 25.

A double-pole, single throw record switch 6 is connected, when in its on position, to provide power from light source batteries 24 to the light source 22. The light source 22 is an essentially monochromatic light source, that is, the light source has a peak about a particular wavelength and the other wavelength components produced by the light source fall off rapidly from the peak wavelength. Thus, practically, the light source functions as a monochromatic light source. Preferably, a green light emitting diode which emits green light having a wavelength of about 550 nanometers is used as the light source 22. It has been found that the green light minimizes the effects of outside (ambient) light on the photodiode 26. The light source 22 is connected in series with one pole of switch 6 across the light source batteries 24. The second pole of record switch 6 is connected between the wiper 15 of meter calibration control 16 and the meter 14.

Light receptor bandwidth control potentiometer 18 has its poles connected across pins 1 and 5 of the amplifier 25. Its wiper 29 is connected to pin 4 of the amplifier 25, as well as to one pole of master switch 5, as previously described.

A feedback circuit comprised of two series-connected resistors 28 and 30 and a capacitor 32 shunted across the second resistor 30, is connected between the output and one input of the amplifier 25. Typically, the two resistors 28 and 30 have values of 2.7 kilohms and 10 megohms and the capacitor 32 a value of 0.01 microfarads. The purpose of the feedback circuit is to protect the meter 14 from being overdriven by the output of the amplifier 25. This is accomplished by limiting the output available at the output of the amplifier to the full meter deflection current of 50 microamps.

In operation, the present invention functions as follows. First, the main power switch 5 and the light receptor power switch 4 are turned to their on positions. This provides electrical current to all of the circuitry, except the LED 22. Record switch 6, which may be a momentary contact push-button switch, is then depressed and the potentiometer 18 is utilized to obtain a 50 microamp or full meter deflection of meter 14. The use of potentiometer 18 to set the bandwidth of the photodiode 26 output is ordinarily necessary only for the setting of the device at the place of manufacture. Thereafter, it is not normally necessary to adjust this bandwidth control 18.

Since the bandwidth control 18 has been set at the place of manufacture, the salesperson need only, after turning on switches 4 and 5, insert a clean or "master" probe into the slot 8 and depress the probe button record switch 6. This causes the LED 22 to emit a green light which passes through the clean probe and is received by the photodiode 26. The photodiode 26 produces an output current proportional to the amount of light received. This output is amplified by the amplifier 25 whose output is fed to the meter 14. Meter calibration control potentiometer 16 is then adjusted by the salesperson such that the meter reading is zero or "dry". The device is thus fully calibrated and ready for use.

In operation, to determine an individual's skin type, power switches 4 and 5 are first placed in their on positions. Then a clear probe is pressed to the skin of the individual, for example, behind the ear, at which time an oil sample is picked up. The oil sample-containing probe 10 is then inserted into the slot 8 and the record switch 6 is depressed to actuate the LED 22. Green light is emitted which passes through the probe 10. The photodiode 26 detects the amount of light which passes through the oil sample carried by the probe 10 and produces an output current proportional thereto. Since the oil sample on the probe 10 offers less resistance to light transmission therethrough than a clean probe, the resistance of the photodiode 26 will decrease and the output current from the photodiode 26 will increase. This output is fed to amplifier 25 which then drives the meter 14 to indicate the type of skin of the tested individual.

If desired, the record switch 6 could be actuated directly by the insertion of the probe 10 in the slot 8, instead of by means of a separate switch.

In addition to the 550 nanometer wavelength light source disclosed herein, other wavelengths of light can be utilized, as disclosed more fully in commonly assigned, co-pending application Ser. No. 472,548, filed concurrently herewith entitled "Improved Device For Determining Skin Type", the subject matter of which is incorporated herein by reference.

Although only a preferred embodiment is specifically illustrated and described herein, it will be appreciated that many other modifications and variations of the present invention are possible in light of the above teachings and within the purview of the appended claims without departing from the spirit and intended scope of the invention.

What is claimed is:

1. A device for determining the skin type of a living subject utilizing an oil sample taken from the skin of the subject and held on a probe capable of permitting light to pass therethrough, comprising:
   means for impinging essentially monochromatic light on one side of said probe;
   means for detecting that portion of the impinging light which is transmitted entirely through said probe, said detecting means producing an output current proportional to the amount of light detected;
   means for displaying the skin type of said living subject as a function of said output current; and
   slot means for receiving said probe, said means for impinging essentially monochromatic light and said means for detecting being located on opposite sides of said slot whereby said essentially monochromatic light passes through said probe without substantial deviation.

2. The device of claim 1, wherein said means for displaying comprises an amplifier connected to receive said output current from said means for detecting and meter display means connected to the output of said amplifier.

3. The device of claim 1 or 2, wherein said essentially monochromatic light is green light of about 550 nanometers.

4. The device of claim 3, further including calibration means connected such that the means for displaying can be adjusted to display a predetermined reading when a probe without an oil sample thereon is utilized in place of an oil sample containing probe.

5. The device of claim 3, wherein said light detecting means is positioned on the side of said probe opposite said impinging light means.

6. The device of claim 3, further including feedback circuit means connected between an input and the output of said amplifier for preventing overloading of said meter display means.

7. The device of claim 3, further including bandwidth adjusting means for said means for detecting, connected to said amplifier means such that the output of said amplifier means can be adjusted, in accordance with the operational characteristics of said means for detecting, to produce a bandwidth equal to the deflection scale of said meter display means.

8. The device of claim 1, further including calibration means connected such that the means for displaying can be adjusted to display a predetermined reading when a probe without an oil sample thereon is utilized in place of an oil sample containing probe.

9. The device of claim 8, further including feedback circuit means connected between an input and the output of said amplifier for preventing overloading of said meter display means.

10. The device of claim 9, further including bandwidth adjusting means for said means for detecting, connected to said amplifier means such that the output of said amplifier means can be adjusted, in accordance to the operational characteristics of said means for detecting, to produce a bandwidth equal to the deflection scale of said meter display means.

11. The device of claim 10 wherein said essentially monochromatic light is green light of about 500 nanometers.

12. A method of calibrating a device for determining the skin type of a living subject, which device utilizes an oil sample taken from the skin of the subject held on a probe capable of permitting light to pass therethrough and slot means for receiving the probe, comprising the steps of:

inserting a probe which is free of oil in said slot means;

impinging essentially monochromatic light on the probe on one side of said slot means;

detecting that portion of said impinging essentially monochromatic light which is transmitted through said probe on the side of said slot means opposite which said monochromatic light is impinged;

producing an output current proportional to the amount of the detected light;

amplifying said output current and applying the amplified signal to display means; and adjusting the amplification of said output current to produce a predetermined desired reading on said display means.

13. The method of claim 12, further including the step of adjusting the bandwidth of said amplified signal to coincide with the bandwidth of said display means.

14. The method of claim 12, wherein said essentially monochromatic light is a green light having a wavelength of about 550 nanometers.

15. A method for determining the skin type of a living subject, which device utilizes an oil sample taken from the skin of the subject held on a probe capable of permitting light to pass therethrough and slot means for receiving said probe, comprising the steps of:

obtaining an oil sample taken from the skin of the subject on a probe;

inserting said probe in said slot means;

impinging essentially monochromatic light on the probe on one side of said slot means;

detecting that portion of said impinging essentially monochromatic light which is transmitted entirely through said probe on the side of said slot means opposite which said monochromatic light is impinged;

producing an output current proportional to the amount of the detected light;

displaying said output current to indicate the type of skin of the subject being tested.

16. The method of claim 15, wherein said essentially monochromatic light is green light of about 550 nanometers.

* * * * *